United States Patent [19]

Munari et al.

[11] Patent Number: 5,759,234
[45] Date of Patent: Jun. 2, 1998

[54] METHOD AND DEVICE FOR THE INJECTION OF LIQUID SAMPLES IN A GAS CHROMATOGRAPH

[75] Inventors: Fausto Munari, Milan; Pier Albino Colombo, Treviglio, both of Italy; Konrad Grob, Fehraltorf, Switzerland

[73] Assignee: Thermoquest Italia, S.p.A., Rodano, Italy

[21] Appl. No.: 768,960

[22] Filed: Dec. 18, 1996

[30] Foreign Application Priority Data

May 8, 1996 [IT] Italy ................ MI96 A 0916

[51] Int. Cl.[6] ................................ B01D 15/08
[52] U.S. Cl. ............. 95/14; 95/18; 95/87; 95/89; 96/102; 96/105
[58] Field of Search ............... 73/23.22, 23.25, 73/23.27, 23.29, 23.36; 95/14, 15, 18, 19, 22, 23, 82, 87, 89; 96/101, 102, 105

[56] References Cited

U.S. PATENT DOCUMENTS

| 4,699,768 | 10/1987 | Weiss | 96/101 X |
|---|---|---|---|
| 4,805,441 | 2/1989 | Sides et al. | 95/87 X |
| 4,948,389 | 8/1990 | Klein et al. | 96/102 X |
| 4,976,750 | 12/1990 | Munari | 95/19 |
| 5,108,466 | 4/1992 | Klein et al. | 94/14 X |
| 5,133,859 | 7/1992 | Frank et al. | 96/102 X |
| 5,160,765 | 11/1992 | Rotman et al. | 427/229 |
| 5,163,979 | 11/1992 | Patrick et al. | 96/102 X |
| 5,391,221 | 2/1995 | Fukushima et al. | 96/102 X |
| 5,405,432 | 4/1995 | Snyder et al. | 95/87 X |
| 5,431,712 | 7/1995 | Henderson et al. | 96/102 X |
| 5,467,635 | 11/1995 | Nakagawa et al. | 95/19 X |
| 5,476,000 | 12/1995 | Henderson et al. | 95/15 X |
| 5,531,959 | 7/1996 | Johnson et al. | 96/102 X |
| 5,545,252 | 8/1996 | Hinshaw et al. | 96/102 X |
| 5,588,988 | 12/1996 | Gerstel et al. | 96/101 |
| 5,642,278 | 6/1997 | Wang et al. | 96/102 X |

FOREIGN PATENT DOCUMENTS

| 0 551 847 A1 | 7/1993 | European Pat. Off. |
| 40 11 350 A1 | 10/1991 | Germany. |
| 43 16 375 C1 | 6/1994 | Germany. |
| WO 94/28409 | 12/1994 | WIPO. |

OTHER PUBLICATIONS

Konrad Grob, *Development of the transfer techniques for on–line high–performance liquid chromatography—capillary gas chromatography*, Journal of Chromatography A, 1995; pp. 265–276.

Jeroen C. Bosboom, Hans–Gerd Janssen, Hans G.J. Mol & Carel A. Cramers, *Large–volume injection in capillary gas chromatography using a programmed–temperature vaporizing injector in the on–column or solvent–vent injection mode*, Journal of Chromatography A, 1996; pp. 384–391.

Hans G.J. Mol, Hans–Gerd Janssen, Carel A. Cramers & Udo A.Th. Brinkman, *Large–volume injection in gas chromatographic trace analysis using temperature–programmable (PTV) injectors*, Trends in Analytical Chemistry, vol. 15, No. 4, 1996; pp. 206–214.

*Primary Examiner*—Robert Spitzer
*Attorney, Agent, or Firm*—Cobrin Gittes & Samuel

[57] ABSTRACT

The invention relates to a method and a device to control the physical conditions of the solvent within a pre-column, in a gas chromatography analysis apparatus. To achieve desired and controlled conditions of recondensation in the pre-column with vaporization injectors or of vaporation with "on-column" injectors, the dew-point of the solvent in the pre-column is calculated and the factors which influence this dew-point are varied and/or the temperature of the pre-column is varied, in order to set such temperatures in a desired correlation.

27 Claims, 2 Drawing Sheets

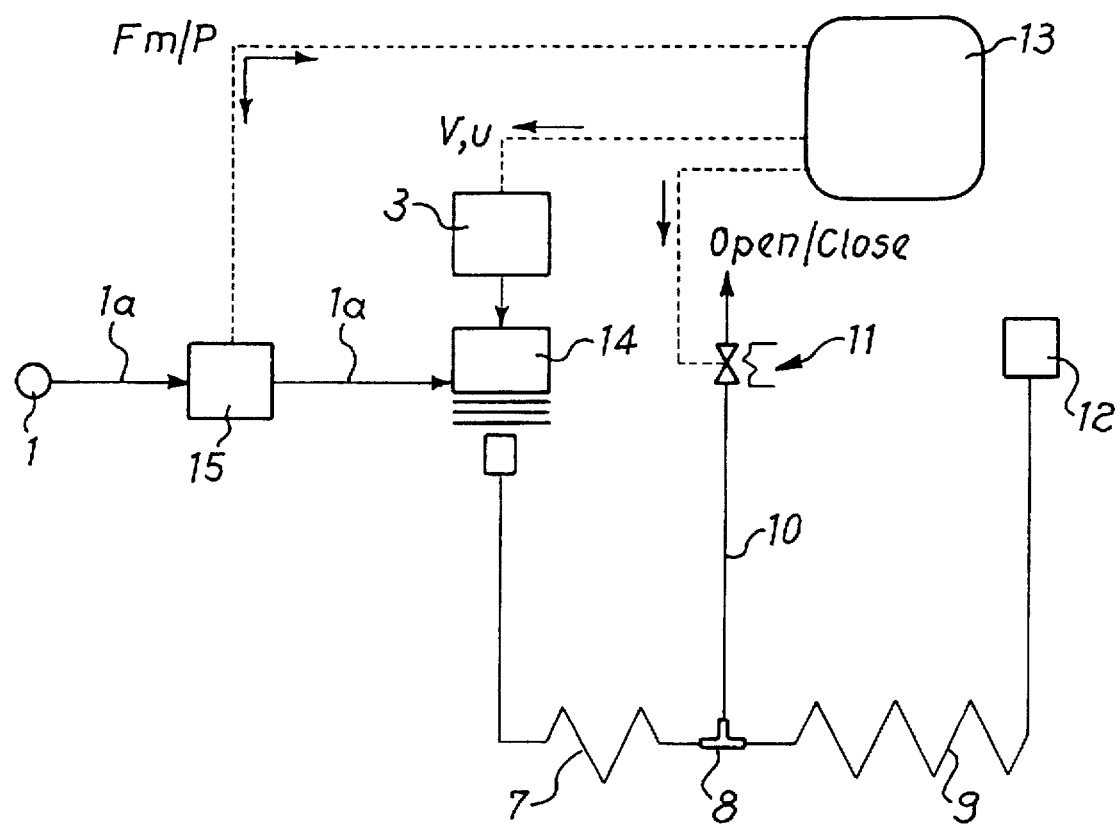

METHOD AND DEVICE FOR THE INJECTION OF LIQUID SAMPLES IN A GAS CHROMATOGRAPH

BACKGROUND OF THE INVENTION

The present invention relates to a method and a device for the injection of liquid samples, particularly of high volumes of samples, into gas chromatography columns, especially capillary columns.

FIELD OF THE INVENTION

The introduction of samples in a GC capillary column involves substantially two steps: the evaporation of the solvent and its separation from the compounds of interest, which must be subsequently evaporated and sent to the GC column, while the solvent vapors are vented, often before passing to the GC column, without at the same time losing the volatile compounds of interest in the sample.

There is a version of the known "on-column" technique in which the sample is injected directly into a pre-column not containing static phase ("retention gap") fitted upstream of the GC column, where the sample is evaporated either simultaneously with or subsequently to its arrival. Most of the evaporated solvent is vented before entering the GC column.

Vaporization injectors are also known (equipped with vaporization chambers) which could also be of the PTV type. In these injectors the initial temperature is fixed and maintained at a value regulated for the evaporation of the solvent. The evaporated solvent is eliminated through a "splitting" exit and therefore the chamber is heated to a higher temperature to vaporize the compounds present in it.

A drawback of these techniques is the possible loss of the volatile compounds together with the solvent vapors. Various forms of injection have been conceived to avoid this eventuality; all have attempted to control somehow the physical state of the solvent, that is the degree of evaporation of the same.

A technique is known which provides for the injection of the sample into a pre-column ("retention gap") maintained at such a temperature as to allow partial evaporation of the solvent during injection and thus create the "solvent effect." This solution is not, however, feasible when the solvent is of the non-wetting type, i.e. which doesn't form a layer on the walls of the pre-column.

Other problems met with using these techniques are those due to the presence in the sample of non-volatile compounds, which degrade and pollute the pre-column.

Alternatively, it has been proposed to inject the sample into a vaporization chamber containing packing, at a temperature higher than the boiling point of the solvent and with such speed as to ensure the vaporization of such solvent. This solution has not proven fully satisfactory due to loss of volatile compounds and difficulty in vaporizing high-boiling-point compounds.

OBJECTS OF THE INVENTION

The aim of the present invention is to resolve the above mentioned problems by a method for introducing liquid samples into a capillary GC column which allows the solvent vapors to be eliminated with reduced loss of compounds of interest, which avoid pollution of the GC column and which make it possible to analyse samples with "non-wetting" solvents.

Another purpose of the invention is to control the conditions of the solvent in the pre-column to get the required degree of recondensation of the vapors in the same, in the case of vaporization injection, or the required form of vaporization in the same pre-column in the case of "on-column" injection.

Yet another purpose of the invention is to provide a device to effect the above method.

SUMMARY OF THE INVENTION

Such purposes are achieved by the present invention, which relates to a method for the injection to vaporization of liquid samples into a gas chromatograph, characterized according to Claim 1.

The invention also relates to a device for introducing liquid samples into a gas chromatograph, characterized according to Claim 13.

Compared to what has been built or proposed till now by the known technique, the present invention provides for the calculation of the dew-point of the solvent vapors in the pre-column and the regulation of the temperature of the pre-column in relation to the dew-point, or, vice versa, the regulation of factors which influence the dew-point in relation to the temperature of the pre-column, to control the conditions of supply of the solvent vapors.

By "dew-point" is understood the temperature of the change of state of the solvent vapors under the conditions current in the pre-column, including the solvent vapor/carrier gas ratio, temperatures which depend on various parameters, as will be shown later. By the term "pre-column" is understood a true pre-column, separate from the gas chromatography column, or an initial tract of the same gas chromatography column.

In other words, according to the invention the physical state of the solvent in the pre-column is controlled by acting on the temperature of the pre-column as far as is allowed by the chromatographic criteria and/or on the factors which influence the dew-point, varying either one and/or the others in relation to the required physical state of the solvent.

Thus it is possible to obtain more or less partial recondensation of the solvent vapors in the pre-column downstream of the vaporization chamber (for vaporization injectors), or partially concurrent solvent evaporation or fully concurrent solvent evaporation of the solvent in the pre-column into which the sample is injected (for "on-column" type injectors).

The regulation of the dew-point of the solvent to the desired value, depends in general on the following factors: the nature of the solvent, the nature of the carrier gas, the geometric characteristics of the pre-column, the nature and characteristics of the vaporization chamber packing, the geometric characteristics of the vaporization chamber, the temperature of the vaporization chamber, the pressure in the vaporization chamber downstream of the packing, the sample injection-rate, the carrier gas flow-rate. The first six factors are in general predetermined by the geometry of the system and by the materials used, while the other three factors (taking into account that the pressure and the flow-rate of the carrier gas are inter-related) could be varied in a controlled way to give the desired dew-point of the solvent in the pre-column.

In particular, it is advantageous to control the carrier gas flow-rate, which influences the dew-point directly by modifying the partial pressure of the solvent vapors in the pre-column as it varies. The carrier gas is always present, both in the vaporization injectors and with those "on-column", since there is a flow of the same during all phases of the injection of the sample. A smaller or flow of carrier gas corresponds to a smaller dilution of the solvent vapors and will lead to a recondensation of the same (vaporization injector) or to evaporation of the solvent in "partially concurrent" mode ("on-column" injector). Vice versa, increasing the carrier gas flow-rate could prevent recondensation (vaporization injector) or respectively operate in "fully concurrent solvent evaporation" mode ("on-column" injector).

In practice, according to this aspect of the invention, the temperature of the pre-column is set on the basis of the chromatographic requirements and the carrier gas flow-rate is varied (diluting the solvent vapors to a greater or lesser extent) in order to set the dew-point in a predetermined correlation to the temperature set for the pre-column.

It is possible to influence the dew-point by modifying the sample injection-rate, as an alternative to—or jointly with— the variation of the carrier gas flow-rate, which causes variations in the pressure upstream of the pre-column as described.

As well as varying the dew-point, or in alternative to the same, the invention provides for the variation of the pre-column temperature as a function of the dew-point, always to control the physical state of the solvent in the pre-column.

Furthermore, another version of the method according to the invention provides for the flow of the carrier gas being fixed by the operator and, after having calculated the dew-point of the solvent, the temperature of the pre-column downstream of the vaporization chamber, or that part of the pre-column which acts as a vaporization chamber in the case of "on-column" injection, is regulated accordingly.

The control allows, on the basis of the difference between the temperature of the pre-column and the dew point, the desired degree of recondensation or of vaporization in the pre-column to be set and to determine the length of the wet tract in the same.

In a preferred embodiment (for vaporization-type injectors), the sample is evaporated non-selectively i.e. in a way which doesn't evaporate the solvent alone initially and retain the compounds of interest in the vaporization chamber. On the contrary, the solvent vapors and the compounds of interest are separate by the means of retention set downstream of the vaporization chamber, which hold back the compounds to be analyzed and vents the solvent vapors. The retention of the compounds of interest is achieved by recondensing the sample in whole or in part (depending on the injected volume) in a pre-column deprived of stationary phase ("retention gap") which also has a solvent effect retention.

Alternatively or additionally, the compounds of interest are retained in a pre-column containing stationary phase. The pre-column containing stationary phase is maintained at the lowest temperature sufficient to keep the solvent vapors from condensing: in this way "phase soaking" of the stationary phase is achieved which allows the volatile compounds to be held back even in the absence of a solvent effect, i.e. in the absence of liquid solvent. The two techniques could coexist, i.e. an initial recondensation of the vapors of the sample could take place in a pre-column not containing stationary phase, making the vapors flow out of this pre-column through a pre-column containing a stationary phase.

The invention has numerous advantages compared to present technology.

A first advantage is given by it being possible to calculate the dew-point of the solvent and to vary the factors which influence it, thus controlling the same and the temperature of the pre-column in order to achieve the required conditions of recondensation or of vaporization of the solvent in the same pre-column. If it is necessary to operate at a fixed pre-column temperature because of the requirements of the analysis being carried out, the dew-point can be varied in the way indicated above, i.e. by increasing or decreasing the carrier gas flow-rate or modifying one or more of the other factors, particularly the injection-rate, to give more or less partial recondensation or respectively control of the conditions of vaporization of the sample.

Another advantage is given, in the version with vaporizer, by being able to heat the vaporization chamber and the gas chromatograph oven independently and without limits. This allows lower pre-column temperatures than those possible according to the known techniques, while introducing large quantities of liquid sample into the vaporization chamber in a short time.

Another advantage is given by the high percentage of volatile compounds retained and sent to analysis. A further advantage, for the version with vaporizer, is that any non-volatile compounds in the sample remain trapped in the vaporization chamber, without polluting the column or pre-column.

Another advantage (always in the version with vaporization) is that non-wetting liquids can be injected e. g. aqueous solvents and fractions from LC "reversed-phase" analysis.

BRIEF DESCRIPTION OF THE DRAWINGS

The invention will now be described in detail with reference to the enclosed sketches which are illustrative and not limitative, and in which:

FIG. 3 is a scheme of a further embodiment of the invention.

DESCRIPTION OF THE PREFERRED EMBODIMENTS

Figure 1:
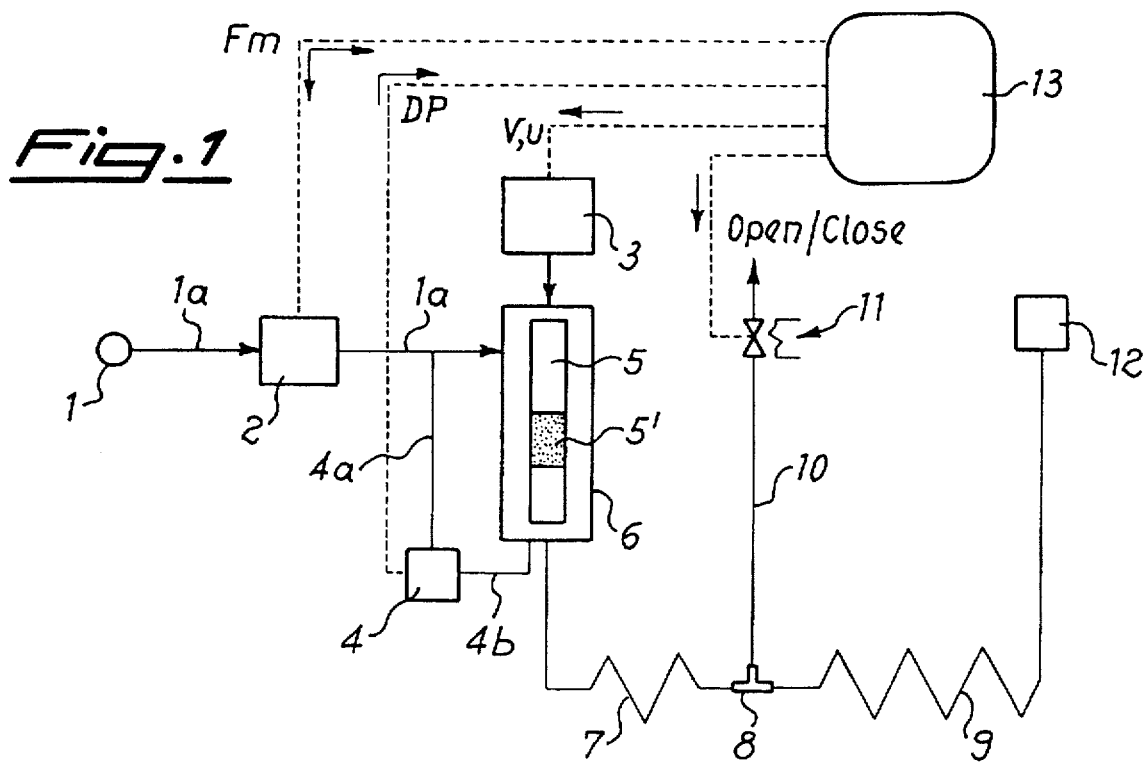
FIG. 1 is a scheme of an embodiment of the device according to the invention.

The device shown in FIG. 1 provides for an injector 6 comprising a solvent vaporization chamber 5 and provided with a packing 5' of inert material for the stabilization of the evaporation of the liquid sample in arrival into the vaporization chamber. The temperature of the chamber 5 is such as to prevent the liquid sample accumulating inside it overflowing and flooding the pre-column 7. In other words, the packing 5' serves as a means of stabilization to avoid violent and uncontrolled evaporation of the solvent and the "shooting" of the same, which is a forward and backward movement of a plug of liquid in the chamber 5, under the effect of the pressure of solvent vapors being formed.

The chamber 5 is connected to an automatic sampler 3, or similar means of control of the injection of the sample, and with a source of carrier gas 1, by means of the line 1a. There is a flow regulator 2 on the line 1a which provides for displaying the value s of the flow of the carrier gas and controlling the same flow-rate and the pressure of the gas. The line 1a is also connected to a sensor 4 by the line 4a, which provides for displaying the pressure difference between the line 1a and the entry of the pre-column 73 downstream of the injector 6, to which it is connected by the line 4b.

The sensor 4, the flow regulator 2 and the means of supplying the sample 3 are connected with means of memorization and data processing 13, by which they are controlled. In the embodiment of FIG. 1 the signal of the carrier gas flow-rate Fm is sent both to the means 13 (IN/OUT) received from, the signal DP of the sensor 4 is sent (INPUT) to the means 13 and the signals V, u relating to the volume of injected sample and to its rate of injection, are sent by the means 13 (OUTPUT) to the means 3 controlling the injection.

The vaporization chamber 5 is provide d with means of heating which are separate and distinct from the means of heating the pre-column 7, which generally comprise the gas chromatograph oven. This configuration reflects the fact that the chamber 5 is generally maintained at a higher temperature than the boiling point of the solvent, for instance at 200° C. at least.

The pre-column 7 does or does not contain stationary phase according to the retention requirements of the solvent which will be applied to it. If partial recondensation of the solvent is required, the pre-column 7 is at least partly deprived of stationary phase, but a portion containing stationary phase is generally scheduled to hold back the compounds at the end of the elimination of the solvent. Alternatively, a tract of pre-column without stationary phase together with another tract of pre-column with stationary phase is predictable.

If there is no recondensation, all the pre-column 7 is prepared with stationary phase.

The pre-column 7 is connected by a T-joint 8 to the separating column 9 and to the line 10 for venting the solvent vapors. The line 10 is fitted with an electrovalve 11, which controls the venting of the vapors. In turn, the electrovalve 11 is connected to the means of data processing 13, from which it receives (OUTPUT) the commands to open or close. A detector 12 is positioned at the end of the separating column 9.

Figure 2:
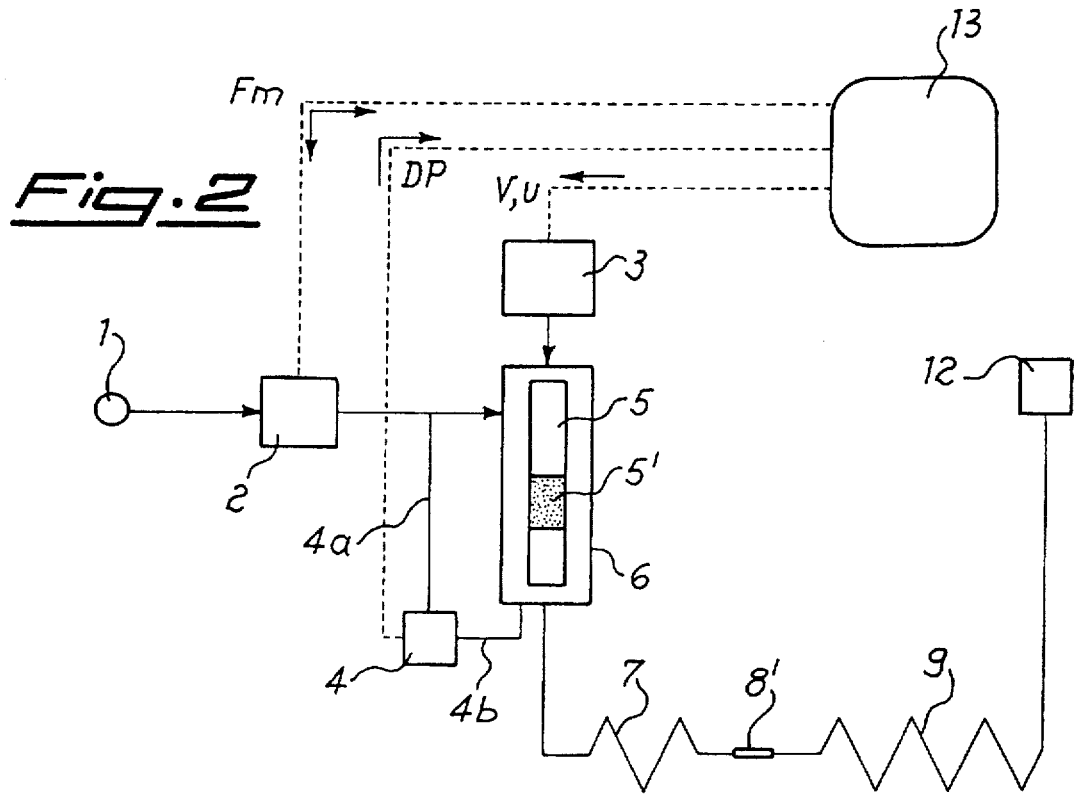
FIG. 2 is a schematic view of a similar embodiment to that of FIG. 1.

FIG. 2 shows an embodiment similar to that of FIG. 1, in which, however, the solvent vapor venting line 10 and the related electrovalve 11 are absent. In this embodiment, the pre-column 7 is joined to the separating column 9 by the joint 8', but can also be constituted by an initial tract of the separating column. Identical components in the two figures are referred to by the same references. This embodiment is used for the injection of samples with not very high volumes and containing volatile compounds of interest with boiling-points very near that of the solvent, in "splitless" mode, i.e. where the solvent vapors are not vented but sent to the column 9.

The embodiments of FIG. 1 and FIG. 2 refer to a device with a vaporization injector, where the solvent and also any compounds of interest are vaporized in the chamber 5, to be subsequently passed to the pre-column 7.

The embodiment of FIG. 3 refers to a similar device to those above but with an "on-column" injector. In this embodiment the sample is injected directly into the pre-column 7, where conditions are controlled to give partial evaporation of the solvent (partially concurrent solvent evaporation) or evaporation simultaneously with introduction (fully concurrent solvent evaporation). Identical components in FIGS. 1 and 2 have retained the same references; unlike the preceding embodiments, in this case the differential pressure sensor 4 is absent and there is an "on-column" injector 14. On the line 1a there are means 15 of measuring and controlling the flow-rate and the pressure of the carrier gas; such means are connected to the computer 13 by IN/OUT to send signals generated by the carrier gas flow-rate and pressure detectors to the means 13 and to receive control signals from the data processing means 13. The means 3 of supplying the sample and the electrovalve 11 are similarly connected to the means 13 as in FIGS. 1 and 2.

The above illustrated devices operate in the following way.

First of all, the mode of operation is decided on, checking the sample to see if it is dirty or contains water. If the answer is in the affirmative, vaporization injection will be opted for, i.e. using the devices of FIG. 1 or 2. If the sample is not dirty and doesn't contain water, "on-column" injection is preferable.

Common to both techniques is the calculation of the dew-point of the solvent in the pre-column 7 and adjustment of the factors which influence this dew-point and/or adjust the temperature of the pre-column on the basis of the required physical state of the solvent inside the pre-column.

As stated above, it is advantageous to control the dew-point of the solvent in the pre-column by acting on the carrier gas flow-rate and, where necessary, on the sample injection-rate. To this end, act as follows: first identify the solvent, the carrier gas and the geometry of the pre-column 7. If in vaporization mode, define and memorize the geometric characteristics of the vaporization chamber 5 and of the packing 5'.

The data is memorized in the means of data processing 13. Then the dew-point of the solvent vapors in the pre-column is calculated, which is a function of the varying injection-rates, of the carrier gas pressure upstream of the pre-column 7 and of flow-rate of carrier gas (these last two are inter-related). As mentioned above, the invention provides for varying the temperature of the pre-column, once the dew-point has been calculated, and/or, vice versa, to get the desired dew-point once the temperature of the pre-column has been fixed, to control recondensation or vaporization in the pre-column 7 which, as has been shown, acts as a possible recondensation chamber in the vaporization mode and as a vaporization chamber in the "on-column" mode.

In the first case (vaporization) the solvent is vaporized in the chamber 5 and the vapors are fed into the pre-column 7. The temperature of the injector 6 and of the chamber 5 could be constant and is selected to guarantee the complete evaporation of the solvent. The vaporization chamber temperature could be programmed i.e. at first, the temperature of the chamber 5 could be such as to vaporize the solvent initially; then this temperature could be raised to vaporize all the volatile compounds present in the sample.

If the sample to be analyzed is aqueous or not aqueous with no volatile compounds of interest, the vapors generated in chamber 5 pass into the pre-column 7 provided with stationary phase where they do not undergo any recondensation. If there are volatile compounds of interest in the sample, the vapors are fed to a pre-column at least partially deprived of stationary phase, where the solvent is recondensed according to the mode calculated or previously set by the operator.

More particularly, there are two possible options in the case of vaporization injection.

In the first case, the flow of carrier gas is set and it is adjusted by the flow regulator 2, sending and receiving a signal corresponding to such flow to and from the data processing means 13. Then, an injection-rate and a temperature of the vaporization chamber 5 are chosen to give complete vaporization of all the usable solvents;

this data is sent by the data processing means 13 to the sampler 3 and to the injector 6. At this point, the injection pressure data is measured, the solvent vapor partial pressure is calculated and from this, for instance by means of a diagram of state, the dew-point of the solvent vapors in the pre-column is calculated.

The temperature of the GC oven, or of the pre-column, is regulated therefore to a desired value, above or below the dew-point. If the temperature of the pre-column is higher than the dew-point, then recondensation does not occur but there is an interaction of the stationary phase with the solvent vapors in such a way as to give a swelling of the stationary phase (phase soaking) to such an extent as to increase the retention power to trap the compounds of interest. If the temperature of the pre-column is below that of the dew-point, a partial recondensation of the solvent in the pre-column deprived of stationary phase will occur, with the possibility of regulating the degree of this recondensation and the length of the wetted tract of the pre-column.

The second solution provides first of all, for fixing the temperature of the pre-column, for setting the type of solvent and the geometry of the pre-column used, choosing between vaporization with recondensation and vaporization without recondensation. Therefore, the means 13 set a vaporization chamber temperature such as to cause complete vaporization of the solvent in the vaporization chamber 5; they calculate the dew-point of the solvent vapors in the pre-column, and they regulate the flow-rate of the carrier gas and/or the injection-rate to give a value of the dew-point such as to cause either partial recondensation or no recondensation of the solvent vapors.

The means 13 calculate the percentage of desired recondensation and the length of the wet tract of pre-column and set the corresponding flow-rate necessary to give the required correlation between dew-point and pre-column temperature.

The above method is also substantially valid for "on-column" injection, with the difference that in the latter case the dew-point depends only on the following factors: the nature of the solvent, the nature of the carrier gas, the injection-rate, the pressure and flow-rate of the carrier gas; the two factors—flow-rate and injection-rate—are those which are advantageously controlled to give the desired dew-point of the solvent in the pre-column 7 (which acts as a vaporization chamber) or to calculate the dew-point in the case where the temperature of the pre-column is regulated. Also here the physical state of the solvent in the pre-column is controlled by acting on the dew-point and/or on the temperature of the pre-column.

We claim:

1. Method for injection of a liquid sample that comprises a solvent and compounds to be analyzed, into a gas chromatograph comprising at least one pre-column, comprising the following steps:

supplying a controlled flow of carrier gas during the injection;

establishing a nature of the solvent, of the carrier gas, and a geometry of the pre-column, memorizing corresponding data by means of data processing;

calculating a dew-point of solvent vapors in said pre-column as a function of the memorized data and of values of injection-rate, of pressure upstream of the pre-column and of a flow-rate of the carrier gas; and carrying out at least one of regulating temperature of said pre-column and modifying at least one of the values which influence the dew-point, to control the physical state of the solvent in said pre-column.

2. Method according to claim 1, wherein the gas chromatograph is further provided with a vaporization chamber, characterized in that the memorizing also involves memorization of data related to the geometry of the vaporization chamber, to the nature of the packing present in this chamber and, optionally, to the temperature in the vaporization chamber.

3. Method according to claim 2, characterized by comprising the following steps:

supplying the carrier gas at controlled flow-rate, sending control signals corresponding to the flow from means of controlling the flow to means of data processing and vice-versa;

setting a vaporization chamber temperature such that all the solvent in the chamber is vaporized;

setting a pre-column temperature;

hypothesizing a desired dew-point for the solvent vapors in the pre-column in relation to the temperature set for the pre-column;

calculating and regulating a flow-rate of at least one of the carrier gas and the injection-rate of the sample so that an actual dew-point corresponds to a desired hypothetical one, to give partial recondensation or no recondensation of the solvent vapors, in relation to the pre-column temperature.

4. Method according to claim 2, characterized by comprising the following steps:

supplying the carrier gas at a controlled flow-rate, sending signals corresponding to the controlled flow from means of controlling the flow to means of data processing and vice-versa;

setting a vaporization chamber temperature to completely vaporize the solvent in the chamber;

calculating a dew-point of the solvent vapors in said pre-column on the basis of at least one of the carrier gas flow-rate and the sample injection-rate, and regulating the temperature of the pre-column in relation to the calculated dew-point, so as to give a partial recondensation or no recondensation of the solvent vapors, in relation to the temperature of the pre-column.

5. Method according to claim 1, characterized by setting a flow-rate of the carrier gas to get a desired dew-point of the solvent in the pre-column, correlated to the temperature of the pre-column in order to give a desired vaporization or recondensation of the solvent in the pre-column.

6. Method according to claim 1, characterized by setting the injection-rate of the sample to give a desired dew-point of the solvent in the pre-column, correlated to the temperature of the pre-column to give either vaporization or recondensation of the solvent in the pre-column.

7. Method according to claim 1, wherein the gas chromatograph is equipped with an "on-column" injector, characterized by comprising the following steps: supplying the carrier gas at a controlled flow, sending signals corresponding to the controlled flow from means of controlling the flow to means of data processing and vice versa;

setting a pre-column temperature;

hypothesizing a desired dew-point of the solvent vapors in pre-column, in relation to the temperature set for the pre-column;

calculating and regulating flow of at least one of carrier gas and an injection rate of the sample so that an actual dew-point temperature corresponds to that hypothesized, to achieve controlled vaporization of the solvent vapors, in relation to the temperature of the pre-column.

8. Method according to claim 1, wherein the gas chromatograph is equipped with an "on-column" injector, characterized by the comprising the following steps:

supplying the carrier gas at a controlled flow rate, sending signals corresponding to flow from means of controlling the flow to means of data processing and vice-versa;

calculating the dew-point of the solvent vapors in the pre-column on the basis of at least one of the carrier gas flow-rate of and the sample injection-rate; and regulating the temperature of said pre-column in relation to a temperature of the dew-point to give controlled vaporization of the solvent vapors, in relation to the temperature of the pre-column.

9. Method according to claim 1, characterized by feeding the liquid sample onto a pre-column deprived of stationary phase.

10. Method according to claim 9, characterized by separating the compounds to be analyzed from the solvent vapors.

11. Method according to claim 10, wherein the step of separating is carried out by recondensing part of the solvent vapors.

12. Method according to claim 10, wherein the step of separating is carried out in an initial tract of the pre-column deprived of stationary phase.

13. Method according to claim 10, wherein the step of separating is carried out by supplying the sample to a tract of the pre-column prepared with stationary phase.

14. Method according to claim 10, wherein the step of separating is carried out by a solvent controlled vaporization.

15. Method according to claim 1, characterized by controlling the correlation between temperature of the pre-column and dew-point in the same, to give predetermined conditions of any one of recondensation and vaporization, and a predetermined wetted tract of the pre-column.

16. Method according to claim 1, wherein the pre-column is separated from a column of the gas chromatograph.

17. Method according to claim 1, wherein said pre-column constitutes an initial tract of a column of the gas chromatograph.

18. Device for injection of a liquid sample that comprises a solvent and compounds to be analyzed, into a gas chromatograph, comprising at least one pre-column, means for memorizing a nature of the solvent used, a nature of a carrier gas, and a geometry of the pre-column;

means for measuring and controlling an injection-rate of the liquid sample and a pressure upstream of the pre-column;

means for measuring and controlling a flow-rate of the carrier gas;

means for measuring and controlling a temperature of the pre-column; and means for memorizing and processing data to calculate a dew-point of the solvent in the pre-column and to regulate at least one of the dew-point and the pre-column temperature to give a required physical state of the solvent in the pre-column.

19. Device according to claim 18, further comprising a solvent vaporization chamber, means for memorizing data related to geometry of the vaporization chamber and to a nature of packing present in said vaporization chamber, means for measuring a temperature of the vaporization chamber and means for measuring a difference in pressure of the carrier gas upstream and downstream of the vaporization chamber.

20. Device according to claim 19, further comprising means for heating said vaporization chamber and said pre-column separately.

21. Device according to claim 18, characterized in that the pre-column is at least partially deprived of a stationary phase.

22. Device according to claim 21, characterized in that the pre-column is at least partially prepared with stationary phase.

23. Device according to claim 18, further comprising a vaporization-type injector for injecting the liquid sample into the gas chromatograph.

24. Device according to claim 18, further comprising an "on-column"-type injector for injecting the liquid sample into the gas chromatograph.

25. Device according to claim 18, wherein the pre-column is separate from a column of the gas chromatograph.

26. Device according to claim 18, wherein the pre-column constitutes an initial tract of a column of the gas chromatograph.

27. Device for injection of a liquid sample that comprises a solvent and compounds to be analyzed, into a gas chromatograph, the device comprising;

at least one pre-column;

means for memorizing a nature of the solvent used, a nature of the carrier gas, and a geometry of the pre-column;

means for measuring and controlling an injection-rate of the liquid sample a pressure upstream of the pre-column, a flow-rate of the carrier gas, and a temperature of the pre-column; and means for memorizing and processing data to calculate a dew-point of the solvent in the pre-column and to regulate at least one of the dew-point and the pre-column temperature to give a required physical state of the solvent in the pre-column.

* * * * *